United States Patent [19]

Lorenz et al.

[11] 4,127,653

[45] Nov. 28, 1978

[54] O-ALKYL-6-CHLORO-BENZISOXAZOL-(3)-YL-THIONOPHOSPHORIC (PHOSPHONIC) ACID ESTERS

[75] Inventors: Walter Lorenz, Wuppertal; Ingeborg Hammann, Cologne; Wolfgang Behrenz, Overath-Steinenbrueck; Bernhard Homeyer, Leverkusen; Wilhelm Stendel, Wuppertal, all of Germany

[73] Assignee: Bayer Aktiengesellschaft, Leverkusen, Germany

[21] Appl. No.: 849,295

[22] Filed: Nov. 7, 1977

Related U.S. Application Data

[63] Continuation of Ser. No. 669,797, Mar. 24, 1976, abandoned.

[30] Foreign Application Priority Data

Apr. 11, 1975 [DE] Fed. Rep. of Germany ....... 2515793

[51] Int. Cl.² ........................... A01N 9/28; C07F 9/65
[52] U.S. Cl. ............................. 424/200; 260/307 DA
[58] Field of Search ................. 260/307 DA; 424/200

[56] References Cited

U.S. PATENT DOCUMENTS

| 3,232,951 | 2/1966 | Lorenz | 260/304 |
| 3,828,063 | 8/1974 | Lorenz et al. | 260/307 D |
| 3,908,005 | 9/1975 | Lorenz et al. | 424/200 |
| 3,914,243 | 10/1975 | Lorenz et al. | 260/307 D |

*Primary Examiner*—Raymond V. Rush
*Attorney, Agent, or Firm*—Sprung, Felfe, Horn, Lynch & Kramer

[57] ABSTRACT

O-Alkyl-6-chloro-benzisoxazol-(3)-yl-thionophosphoric (phosphonic) acid esters of the formula

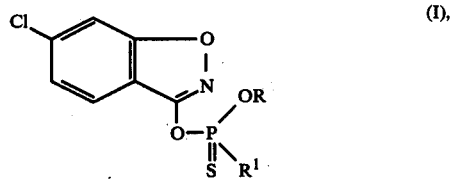

in which
R is alkyl with 1 to 4 carbon atoms and
$R^1$ is alkyl with 1 to 3 carbon atoms or alkoxy with 1 to 4 carbon atoms, which possess insecticidal, acaricidal, nematicidal and fungicidal properties.

7 Claims, No Drawings

O-ALKYL-6-CHLORO-BENZISOXAZOL-(3)-YL-THIONOPHOSPHORIC (PHOSPHONIC) ACID ESTERS

This is a continuation of application Ser. No. 669,797, filed Mar. 24, 1976, now abandoned.

The present invention relates to and has for its objects the provision of particular new O-alkyl-6-chlorobenzisoxazol-(3)-yl-thionophosphoric(phosphonic) acid esters, i.e. O,O-dialkyl-6-chloro-benzisoxazol-(3)-yl-thionophosphoric acid esters and O-alkyl-6-chloro-benzisoxazol-(3)-yl-thionoalkanephosphonic acid esters, which possess insecticidal, acaricidal, nematicidal or fungicidal properties, active compositions in the form of mixtures of such compounds with solid and liquid dispersible carrier vehicles, and methods for producing such compounds and for using such compounds in a new way especially for combating pests, e.g. insects, acarids, nematodes, and fungi with other and further objects becoming apparent from a study of the within specification and accompanying examples.

It is known from German Published Specification DAS No. 1,253,713 and Netherlands Patent Application No. 7,305,731 that 5-chloro- and 7-chloro-benzisoxazole-thionophosphoric(phosphonic) acid esters, for example O,O-dimethyl-O-[5-chloro-(Compound A) or -7-chloro-benzisoxazol-(3)-yl]-(Compound B) or O,O-diethyl-O-[5-chlorobenzisoxazol-(3)-yl]-thionophosphoric acid ester (Compound C), or O-ethyl-O-[7-chloro-benzisoxazol-(3)-yl]-thionoethanephosphonic acid ester(Compound D), have an insecticidal and acaricidal action.

The present invention provides, as new compounds, the 6-chlorobenzisoxazole-thionophosphoric(phosphonic) acid esters of the general formula

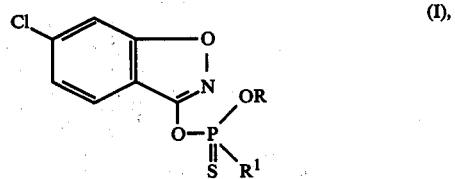

in which
R is alkyl with 1 to 4 carbon atoms and
R$^1$ is alkyl with 1 to 3 carbon atoms or alkoxy with 1 to 4 carbon atoms.

Preferably, R represents straight-chain or branched alkyl with 1 to 3 carbon atoms, viz. methyl, ethyl, n-propyl, or isopropyl, and R$^1$ represents methyl, ethyl or straight-chain or branched alkoxy with 1 to 3 carbon atoms, viz. methoxy, ethoxy, n-propoxy and iso-propoxy.

Surprisingly, the 6-chlorobenzisoxazole-thionophosphoric(phosphonic) acid esters according to the invention exhibit a better insecticidal, acaricidal and nematicidal action than corresponding 5- and 7-chloro-derivatives of analogous structure and of the same type of action. The compounds according to the present invention thus represent a genuine enrichment of the art.

The invention also provides a process for the preparation of a 6-chlorobenzisoxazole-thionophosphoric(-phosphonic) acid ester of the formula (I) in which 6-chloro-3-hydroxy-benzisoxazole, which has the formula

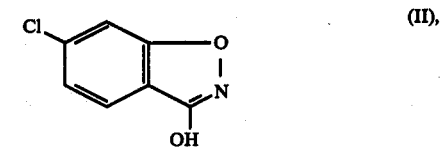

is reacted as such, in the presence of an acid acceptor, or in the form of an alkali metal salt, alkaline earth metal salt or ammonium salt thereof, with a thionophosphoric(phosphonic) acid ester halide of the general formula

in which
R and R$^1$ have the above-mentioned meanings and
Hal represents halogen, preferably chlorine, optionally in the presence of a solvent or diluent.

If O,O-di-n-butylthionophosphoric acid diester chloride and 6-chloro-3-hydroxy-benzisoxazole are used as starting materials, the course of the reaction can be represented by the following equation:

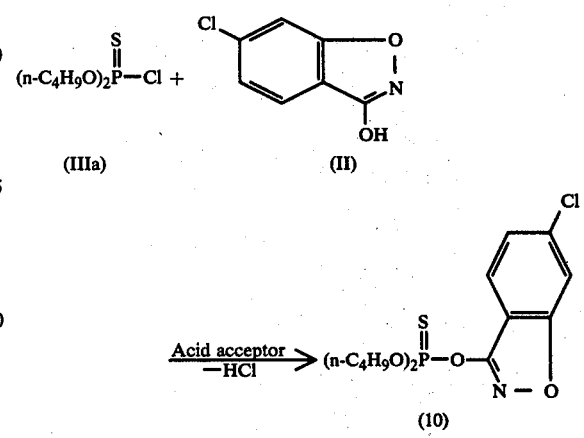

The thionophosphoric(phosphonic) acid ester halides (II) required as starting materials are known and can be prepared in accordance with customary processes. 6-Chloro-3-hydroxybenzisoxazole is also known [see Chem. Ber. 100, pages 954,960 (1967)].

The following may be mentioned as examples of the thionophosphoric(phosphonic) acid ester halides (III) which can be used as starting materials: O,O-dimethyl-, O,O-diethyl-, O,O-di-n-propyl, O,O-di-iso-propyl-, O,O-di-n-butyl-, O,O-di-iso-butyl-, O,O-di-sec.-butyl-, O,O-di-tert.-butyl-, O-methyl-O-ethyl-, O-methyl-O-n-propyl-, O-ethyl-O-iso-propyl-, O-ethyl-O-sec.-butyl- and O-n-propyl-O-n-butyl-thionophosphoric acid diester chlorides and O-methyl-, O-ethyl-, O-n-propyl-, O-iso-propyl-, O-n-butyl-, O-iso-butyl-, O-sec.-butyl- and O-tert.-butyl-methane-, -ethane-, n-propane- and -iso-propane-thionophosphonic acid ester chlorides.

The process for the preparation of the compounds according to the invention is preferably carried out in the presence of a suitable solvent or diluent. As such it is possible to use practically all inert organic solvents, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 120° C., preferably at from 40° to 60° C.

The reaction is in general allowed to take place under normal pressure.

To carry out the process, the 6-chloro-3-hydroxybenzisoxazole is preferably employed in 10–20% excess. The reaction is preferably carried out in a solvent in the presence of an acid acceptor, in most cases at an elevated temperature. At the end of the reaction time, the reaction mixture is poured into water and is extracted by shaking with an organic solvent, for example toluene. The organic phase is washed and dried and the solvent is distilled off.

The new compounds are frequently obtained in the form of oils which in most cases cannot be distilled without decomposition but are freed from the last volatile constituents by so-called "slight distillation", that is to say by prolonged heating under reduced pressure to moderately elevated temperatures, and are purified in this way. They may be characterized by the refractive index. Some compounds are obtained in a crystalline form and may be characterized by their melting point.

The 6-chlorobenzisoxazole-thionophosphoric(phosphonic) acid esters according to the invention are distinguished by a low phytotoxicity and by an excellent action against sucking and biting insects and against spider mites.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidus = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aëdes aegypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus articae*) and the European red mite (*Paratetranychus pilous* = *Panonychus ulmi*), gall mites, for example the black currant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the present compounds are also distinguished by an outstanding residual activity on wood and clay, as well as a good stability to alkali on limed substrates.

The active compounds according to the invention couple a low toxicity to warm-blooded animals with powerful nematicidal properties and can therefore be used to combat nematodes, especially phytopathogenic nematodes. These essentially include leaf nematodes (Arphelenchoides), such as the chrysanthemum eelworm (*A. ritzemabosi*), the leafblotch eelworm (*A. fragariae*) and the rice eelworm (*A.oryzae*); stem nematodes (Ditylenchus), such as the stem eelworm (*D. Dipsaci*);

root-knot nematodes (Meloidogyne), such as *M. arenaria* and *M. incognita;* cyst-forming nematodes (Heterodera), such as the potato cyst eelworm (*H. rostochiensis*) and the beet eelworm (*H. schachtii*); and also free-living root nematodes, for example of the genera Pratylenchus, Paratylenchus, Rotylenchus, Xiphinema and Radopholus.

The compounds according to the invention are not only active against plant pests, pests harmful to health and pests of stored products but also, in the veterinary medicine field, against animal parasites (ectoparasites), such as parasitic fly larvae. Some of them are also fungicidally active.

For these reasons, the compounds according to the invention can be employed successfully as pesticides in plant protection and in the hygiene field, the field of protection of stored products and the veterinary field.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, nematocides and fungicides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids, nematodes and fungi, and more particularly methods of combating insects, acarids and nematodes, which comprises applying to at least one of correspondingly (a) such insects, (b) such acarids, (c) such nematodes, (d) such fungi, and (e) the corresponding habitat thereof, i.e. the locus to be protected, e.g. to a growing crop, to an area where a crop is to be grown or to a domestic animal, a correspondingly combative or toxic amount, i.e. an insecticidally, acaricidally, nematicidally or fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Ceratitis Test

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

1 ml of the preparation of the active compound was pipetted onto a filter paper disc of about 7 cm diameter. This was placed wet over the orifice of a glass vessel in which there were about 30 fruit flies (*Ceratitis capitata*), and was covered with a glass plate.

After the specified periods of time, the destruction was determined as a percentage. 100% Means that all the flies were killed. 0% Means that none of the flies were killed.

The active compounds, the concentrations of the active compounds, the evaluation times and the degree of destruction can be seen from the following table.

Table 1

| (Insects which harm plants) Ceratitis Test | | |
|---|---|---|
| Active compound | Active compound concentration in % | Degree of destruction in % after 1 day |
| [structure with Cl, O, N, S, C$_2$H$_5$, OC$_2$H$_5$] (known (D)) | 0.02<br>0.004<br>0.0008 | 100<br>85<br>0 |
| [structure with Cl, O, N, S, P(OC$_2$H$_5$)$_2$] (2) | 0.02<br>0.004<br>0.0008 | 100<br>100<br>90 |

EXAMPLE 2

Phaedon Larvae Test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all the beetle larvae had been killed whereas 0% means that none of the beetle larvae had been killed.

The active compounds, the concentrations of the active compounds, the evaluation times and the results can be seen from the following table:

Table 2

| (Insects which harm plants) Phaedon larvae test | | |
|---|---|---|
| Active compound | Active compound concentration in % | Degree of destruction in % after 3 days |
| [structure with Cl, O, N, S, P(OCH$_3$)$_2$] (known) (A) | 0.1<br>0.01<br>0.001 | 100<br>100<br>0 |
| [structure with Cl, O, N, S, P(OC$_2$H$_5$)$_2$] (known) (C) | 0.1<br>0.01<br>0.001 | 100<br>100<br>0 |
| [structure with Cl, O, N, S, P(OCH$_3$)$_2$] (1) | 0.1<br>0.01<br>0.001 | 100<br>100<br>100 |
| [structure with Cl, O, N, S, OCH$_3$, OC$_3$H$_7$-iso] (4) | 0.1<br>0.01<br>0.001 | 100<br>100<br>100 |
| [structure with Cl, O, N, S, P(OC$_2$H$_5$)$_2$] (2) | 0.1<br>0.01<br>0.001 | 100<br>100<br>90 |
| [structure with Cl, O, N, S, C$_2$H$_5$, OC$_2$H$_5$] (3) | 0.1<br>0.01<br>0.001 | 100<br>100<br>85 |

EXAMPLE 3

Euscelis Test

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) were sprayed with the preparation of the active compound until dew-moist and were then infested with cicadas (*Euscelis bilobatus*).

After the specified period of time, the degree of destruction was determined in %. 100% Means that all the cicadas had been killed; 0% Means that none of the cicadas had been killed.

The active compounds, the concentrations of the active compounds, the evaluation times and the results can be seen from the table which follows:

Table 3

(Insect which harm plants)
*Euscelis* Test

| Active compound | Active compound concentration in % | Degree of destruction in % after 3 days |
|---|---|---|
| (known) (A) [Cl-benzisoxazole-O-P(OCH$_3$)$_2$] | 0.1<br>0.02<br>0.004 | 100<br>60<br>0 |
| (2) [Cl-benzisoxazole-O-P(OC$_2$H$_5$)$_2$] | 0.1<br>0.02<br>0.004 | 100<br>100<br>100 |
| (7) [Cl-benzisoxazole-O-P(OCH$_3$)(OC$_3$H$_7$-n)] | 0.1<br>0.02<br>0.004 | 100<br>100<br>80 |
| (4) [Cl-benzisoxazole-O-P(OCH$_3$)(OC$_3$H$_7$-iso)] | 0.1<br>0.02<br>0.004 | 100<br>100<br>100 |
| (3) [Cl-benzisoxazole-O-P(C$_2$H$_5$)(OC$_2$H$_5$)] | 0.1<br>0.02<br>0.004 | 100<br>100<br>70 |
| (5) [Cl-benzisoxazole-O-P(OC$_2$H$_5$)(OC$_3$H$_7$-iso)] | 0.1<br>0.02<br>0.004 | 100<br>100<br>70 |

EXAMPLE 4

Tetranychus Test (Resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 4

(Mites which harm plants)
*Tetranychus* test

| Active compound | Active compound concentration in % | Degree of destruction in % after 2 days |
|---|---|---|
| (known) (A) [Cl-benzisoxazole-O-P(OCH$_3$)$_2$] | 0.1 | 0 |
| (7) [Cl-benzisoxazole-O-P(OCH$_3$)(OC$_3$H$_7$-n)] | 0.1 | 90 |
| (4) [Cl-benzisoxazole-O-P(OCH$_3$)(OC$_3$H$_7$-iso)] | 0.1 | 100 |

Table 4-continued (Mites which harm plants)

_Tetranychus_ test

| Active compound | Active compound concentration in % | Degree of destruction in % after 2 days |
|---|---|---|
| 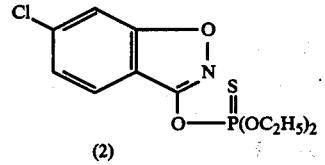 (2) | 0.1 | 85 |
| 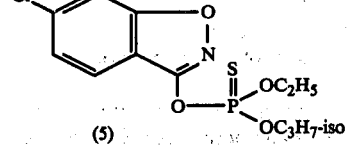 (5) | 0.1 | 100 |

EXAMPLE 5

Critical Concentration Test/Soil Insects

Test insect: _Phorbia antiqua_ grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted herein in ppm (= mg/1). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all the test insects had been killed and was 0% if exactly as many test insects were still alive as in the case of the untreated control.

The active compounds, amounts used and results can be seen from the table which follows:

Table 5

(Soil insecticides)
_Phorbia antioua_ grubs in the soil

| Active compound | Active compound concentration = 20 ppm | Degree of destruction in % |
|---|---|---|
| 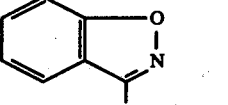 (known) (A) | | 50 |
| 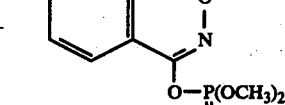 (5) | | 100 |
| 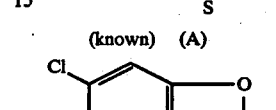 (6) | | 100 |
| 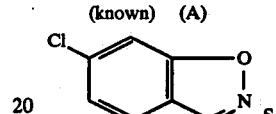 (9) | | 100 |

EXAMPLE 6

Critical Concentration Test/Soil Insects

Test insect: _Tenebrio molitor_ larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted herein in ppm (= mg/1). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all the test insects had been killed and was 0% if exactly as many test insects were still alive as in the case of the untreated control.

The active compounds, amounts used and results can be seen from the table which follows:

Table 6

(Soil insecticides)
*Tenebrio molitor* larvae in the soil

| Active compound | Active compound concentration = 5 ppm | Degree of destruction in % |
|---|---|---|
| 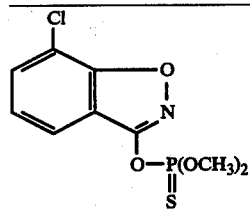 (known) (B) | | 0 |
| 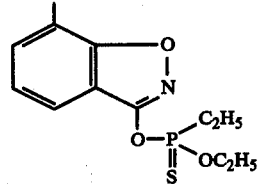 (known) (D) | | 0 |
| 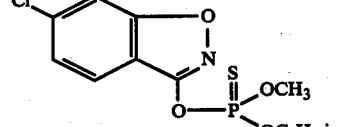 (4) | | 100 |
| 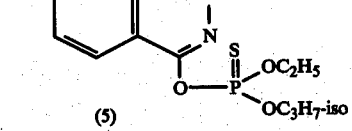 (5) | | 100 |
| 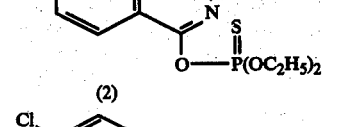 (2) | | 100 |
| 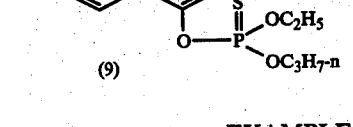 (9) | | 100 |

EXAMPLE 7

Critical Concentration Test

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given herein in ppm, was decisive. The soil was filled into pots, lettuce was sown in and the pots were kept at a greenhouse temperature of 27° C. After 4 weeks, the lettuce roots were examined for infestation with nematodes, and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compounds, the amounts applied and the results can be seen from the following table:

Table 7

(Nematicides)
*Meloidogyne incognita*

| Active compound | Active compound concentration = 10 ppm | Degree of destruction in % |
|---|---|---|
| 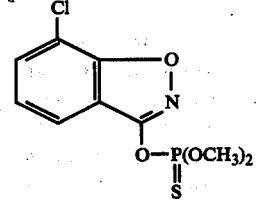 (known) (B) | | 0 |
| 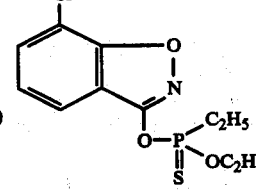 (known) (D) | | 0 |
| 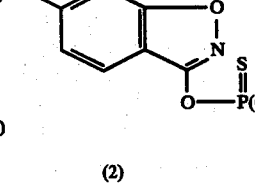 (2) | | 100 |
| 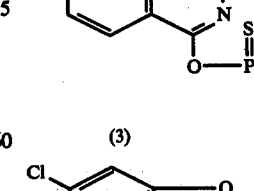 (3) | | 100 |
| 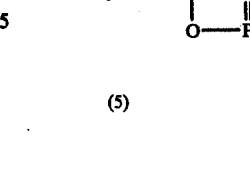 (5) | | 100 |

Table 7-continued

(Nematicides)
*Meloidogyne incognita*

| Active compound | Active compound concentration = 10 ppm | Degree of destruction in % |
|---|---|---|
| Cl-[benzisoxazole]-O-P(=S)(OCH₃)(OC₃H₇-iso) (4) | | 100 |

EXAMPLE 8

LD₁₀₀ Test

Test insects: *Sitophilus granarius*
Solvent: Acetone

2 Parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% Denotes that all test animals had been killed; 0% denotes that no test insects had been killed.

The active compounds, the concentrations of the active compounds, the test insects and the results can be seen from the following table:

Table 8

LD₁₀₀ test

| Active compound | Active compound concentrations % strength solution | Destruction in % |
|---|---|---|
| Cl-[benzisoxazole]-O-P(=S)(OCH₃)₂ (known) (A) | 0.2<br>0.02<br>0.002 | 100<br>100<br>0 |
| Cl-[benzisoxazole]-O-P(=S)(OCH₃)₂ (1) | 0.2<br>0.02<br>0.002 | 100<br>100<br>100 |

Table 8-continued

LD₁₀₀ test

| Active compound | Active compound concentrations % strength solution | Destruction in % |
|---|---|---|
| Cl-[benzisoxazole]-O-P(=S)(OC₂H₅)₂ | 0.2<br>0.02<br>0.002 | 100<br>100<br>100 |
| Cl-[benzisoxazole]-O-P(=S)(OCH₃)(OC₃H₇-iso) (2) | 0.2<br>0.02<br>0.002 | 100<br>100<br>100 |
| Cl-[benzisoxazole]-O-P(=S)(OCH₃)(OC₃H₇-n) (4) | 0.2<br>0.02<br>0.002 | 100<br>100<br>100 |
| Cl-[benzisoxazole]-O-P(=S)(OC₂H₅)(OC₃H₇-n) (7) | 0.2<br>0.02<br>0.002 | 100<br>100<br>100 |
| Cl-[benzisoxazole]-O-P(=S)(OC₂H₅)(OC₃H₇-iso) (9) | 0.2<br>0.02<br>0.002 | 100<br>100<br>100 |
| Cl-[benzisoxazole]-O-P(=S)(C₂H₅)(OC₂H₅) (3) | 0.2<br>0.02<br>0.002 | 100<br>100<br>100 |

EXAMPLE 9

Mosquito Larvae Test

Test insects: *Aëdes aegypti* larvae
Solvent: 99 parts by weight of acetone
Emulsifier: 1 part by weight of benzylhydroxydiphenyl polyglycol ether To produce a suitable preparation of active compound, 2 parts by weight of the active compound were dissolved in 1,000 parts by volume of the solvent containing the amount of emulsifier stated above. The solution thus obtained was diluted with water to the desired lower concentrations.

The aqueous preparations of the active compounds were placed in glass vessels and about 25 mosquito larvae were then placed in each glass vessel.

After 24 hours, the degree of destruction was determined as a percentage. 100% Means that all the larvae were killed. 0% Means that no larvae at all were killed.

The active compounds, the concentrations of the active compounds, the test insects and the results can be seen from the following table:

Table 9

| Mosquito larvae test | | |
|---|---|---|
| Active compound | Active compound concentrations of the solution in ppm | Degree of destruction in % |
| 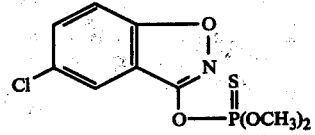 (known) (A) | 1 1.0 0.01 | 100 90 0 |
| 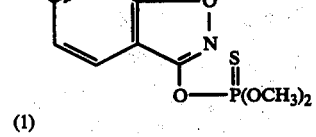 (1) | 0.1 0.01 0.001 | 100 100 90 |
| 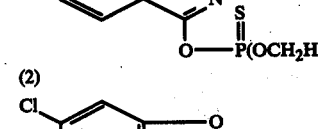 (2) | 0.1 0.01 0.001 0.0001 | 100 100 100 90 |
| 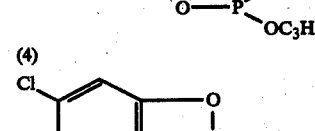 (4) | 0.1 0.01 0.001 | 100 100 80 |
| 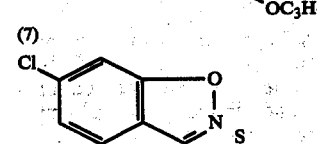 (7) | 0.1 0.01 0.001 | 100 100 80 |
| 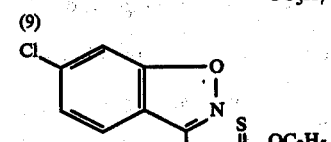 (9) | 0.1 0.01 | 100 90 |
|  (5) | 0.1 0.01 | 100 90 |

EXAMPLE 10

Test with Parasitic Fly Larvae

Solvent: 35 parts by weight of ethylene polyglycol monomethyl ether

Emulsifier: 35 parts by weight of nonylphenol polyglycol ether

To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained approx. 2 cm$^3$ of horse muscle. 0.5 ml of the preparation of active compound was applied to this horse meat. After 24 hours, the degree of destruction in % was determined. 100% Means that all the larvae had been killed and 0% means that no larvae had been killed.

The active compounds investigated, the concentrations of the active compounds used and the results obtained can be seen from the table which follows:

Table 10

| (Test with parasitic fly larvae (*Lucilia cuprina*/resistant)) | | |
|---|---|---|
| Active compound | Active compound concentration in ppm | Degree of destruction in % |
| 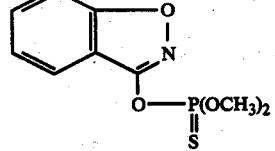 (known) (B) | 100 10 | 100 0 |
| 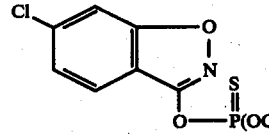 (2) | 1100 30 10 | 100 100 100 |
| 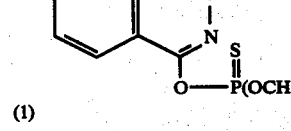 (1) | 100 10 | 100 <50 |
| 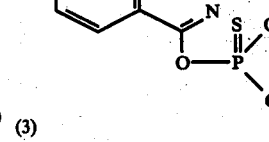 (3) | 100 30 10 | 100 <50 <50 |
| 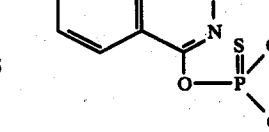 (4) | 100 10 | 100 100 |

Table 10-continued
(Test with parasitic fly larvae (*Lucilia cuprina*/resistant))

| Active compound | Active compound concentration in ppm | Degree of destruction in % |
|---|---|---|
| 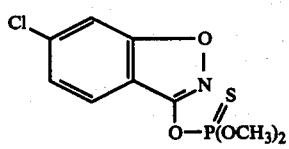 (5) | 100<br>10 | 100<br>100 |
| (similar structure) (6) | 100<br>30<br>10 | 100<br>100<br>100 |
| (similar structure) (7) | 100<br>10 | 100<br>100 |
| (similar structure) (9) | 100<br>10 | 100<br>100 |

The process of the present invention is illustrated by the following preparative example.

EXAMPLE 11

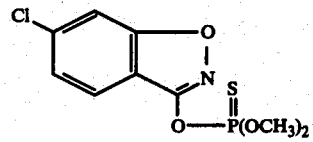
(1)

A mixture of 61 g (0.36 mole) of 6-chloro-3-hydroxybenzisoxazole in 500 ml of acetonitrile and 54 g (0.39 mole) of potassium carbonate was stirred for 30 minutes at 50° C. 48 g (0.3 mole) of O,O-dimethylthionophosphoric acid diester chloride were added dropwise at 50° C. and stirring was continued for a further hour at this temperature and overnight at room temperature. Water was then added and the oil which separated out was taken up in toluene. The organic phase was extracted by shaking with water and then twice with 2 N sodium hydroxide solution and was washed neutral with water. After drying over sodium sulfate, the solvent was distilled off. 63 g (72.5% of theory) of O,O-dimethyl-O-6-chlorobenzisoxazol-(3)-yl-thionophosphoric acid ester were obtained as an oil which on trituration with a petroleum ether/ether mixture (5:1) gave pale yellow, coarse crystals of melting point 37° C.

The following compounds of the formula

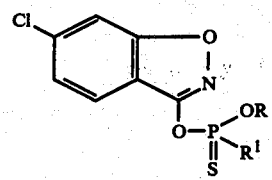
(I)

were prepared analogously:

Table 11

| Compound No. | R | $R_1$ | Physical data (melting point, °C; refractive index) | Yield (% of theory) |
|---|---|---|---|---|
| 2 | —C₂H₅ | —OC₂H₅ | $n_D^{21}$: 1.5365 | 73 |
| 3 | —C₂H₅ | —C₂H₅ | $n_D^{21}$: 1.5565 | 85 |
| 4 | —C₃H₇-iso | —OCH₃ | 45-47 | 62 |
| 5 | —C₃H₇-iso | —OC₂H₅ | $n_D^{21}$: 1.5158 | 65.5 |
| 6 | —C₃H₇-iso | —CC₃H₇-iso | $n_D^{21}$: 1.4792 | 57 |
| 7 | —CH₃ | —OC₃H₇-n | $n_D^{21}$: 1.5383 | 72 |
| 8 | —C₃H₇-n | —OC₃H₇-n | $n_D^{21}$: 1.52225 | 55 |
| 9 | —C₂H₅ | —OC₃H₇-n | $n_D^{21}$: 1.5334 | 75.5 |

It will be appreciated that the instant specification and examples are set forth by way of illustration and not limitation, and that various modifications and changes may be made without departing from the spirit and scope of the present invention.

What we claim is:
1. A compound selected from the group consisting of O,O-dimethyl-O-6-chloro-benzisoxazol-(3)-yl-thiono-phosphoric acid ester and O-ethyl-O-6-chloro-benzisoxazol-(3)-yl-thiono-ethanephosphonic acid ester.
2. The compound according to claim 1, wherein such compound is O,O-dimethyl-O-6-chloro-benzisoxazol-(3)-yl-thiono-phosphoric acid ester of the formula

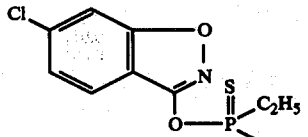

3. The compound according to claim 1, wherein such compound is O-ethyl-O-6-chloro-benzisoxazol-(3)-yl-thiono-ethanephosphonic acid ester of the formula 4. An insecticidal, acaricidal or nematicidal composition containing as active ingredient an insecticidally, acaricidally or nematicidally effective amount of a compound according to claim 1 in admixture with a diluent.
5. A method of combating insects, acarids or nematodes which comprises applying to the insects, acarids or nematodes or to a habitat thereof an insecticidally, acaricidally or nematicidially effective amount of a compound according to claim 1.
6. The method according to claim 5, in which said compound is
O,O-dimethyl-O-6-chloro-benzisoxazol-(3)-yl-thiono-phosphoric acid ester.
7. The method according to claim 5, in which said compound is
O-ethyl-O-6-chloro-benzisoxazol-(3)-yl-thiono-ethanephosphonic acid ester.